United States Patent
Hashimoto et al.

(10) Patent No.: US 9,394,454 B2
(45) Date of Patent: Jul. 19, 2016

(54) POLYCHLOROPRENE LATEX, RUBBER COMPOSITION AND DIP-MOLDED ARTICLE

(75) Inventors: Ikuka Hashimoto, Itoigawa (JP); Hiroyuki Yashima, Itoigawa (JP); Takeo Mori, Itoigawa (JP)

(73) Assignee: DENKA COMPANY LIMITED, Tokyo (JP)

(*) Notice: Subject to any disclaimer, the term of this patent is extended or adjusted under 35 U.S.C. 154(b) by 324 days.

(21) Appl. No.: 14/006,579

(22) PCT Filed: Mar. 29, 2012

(86) PCT No.: PCT/JP2012/058391
§ 371 (c)(1),
(2), (4) Date: Sep. 20, 2013

(87) PCT Pub. No.: WO2012/137663
PCT Pub. Date: Oct. 11, 2012

(65) Prior Publication Data
US 2014/0011936 A1    Jan. 9, 2014

(30) Foreign Application Priority Data
Apr. 6, 2011    (JP) .................... 2011-084819

(51) Int. Cl.
| | |
|---|---|
| *C08L 11/00* | (2006.01) |
| *C09D 111/02* | (2006.01) |
| *C08F 236/18* | (2006.01) |
| *C08K 3/22* | (2006.01) |
| *C08J 5/02* | (2006.01) |
| *A61B 17/00* | (2006.01) |

(52) U.S. Cl.
CPC ............ *C09D 111/02* (2013.01); *C08F 236/18* (2013.01); *C08J 5/02* (2013.01); *C08K 3/22* (2013.01); *A61B 2017/00526* (2013.01); *C08J 2311/02* (2013.01)

(58) Field of Classification Search
CPC ............ C08F 236/18; C08F 2/22; C08J 5/02; C08J 2311/02; C08L 11/00
See application file for complete search history.

(56) References Cited

U.S. PATENT DOCUMENTS

| | | | |
|---|---|---|---|
| 4,338,238 A | 7/1982 | Nolte et al. | 524/706 |
| 8,436,102 B2 | 5/2013 | Hashimoto et al. | 525/250 |
| 2012/0108744 A1 | 5/2012 | Hashimoto et al. | 524/747 |

FOREIGN PATENT DOCUMENTS

| | | |
|---|---|---|
| JP | 56-74108 A | 6/1981 |
| JP | 59-71319 A | 4/1984 |
| JP | 60-65011 A | 4/1985 |
| JP | 2006-307156 A | 11/2006 |
| JP | 2007-106994 A | 4/2007 |
| JP | 2010-126586 A | 6/2010 |
| JP | 2010-144278 A | 7/2010 |
| JP | 2011-122141 A | 6/2011 |
| WO | WO 2011/004805 A1 | 1/2011 |

OTHER PUBLICATIONS

International Search Report mailed Jul. 17, 2012, issued in corresponding International Patent Application No. PCT/JP2012/058391.
Chinese Office Action dated Nov. 14, 2014, issued to Chinese Application No. 201280016960.6.

*Primary Examiner* — Peter D Mulcahy
(74) *Attorney, Agent, or Firm* — Stein IP, LLC

(57) ABSTRACT

Provided is a polychloroprene latex that shows favorable low-temperature stability without deterioration in the rubber agglutinating property during production of the dip-molded article, a rubber composition, and a dip-molded article, prepared by using the same.
Prepared is a polychloroprene latex of a chloroprene copolymer obtained by polymerization of raw monomers at least containing chloroprene and 2,3-dichloro-1,3-butadiene, which is dispersed in water, wherein the 2,3-dichloro-1,3-butadiene content in the raw monomers is controlled to 1 to 30 mass % and the potassium ion content is adjusted to 0.7 to 1.5 parts by mass and the sodium ion content to 0.2 part or less by mass with respect to 100 parts by mass of the solid matter. In addition, a metal oxide: 1 to 10 parts by mass, sulfur: 0.1 to 3 parts by mass, an aging inhibitor: 0.1 to 5 parts by mass and a surfactant: 0.1 to 10 parts by mass, respectively with respect to 100 parts by mass of the solid matter, were added to the chloroprene latex, to give a rubber composition.

12 Claims, No Drawings

POLYCHLOROPRENE LATEX, RUBBER COMPOSITION AND DIP-MOLDED ARTICLE

CROSS-REFERENCE TO RELATED APPLICATIONS

This application is a national stage application of PCT Application No. PCT/JP2012/058391, filed Mar. 29, 2012, which claims the benefit of Japanese Application No. JP 2011-084819, filed Apr. 6, 2011, in the Japanese Patent Office. All disclosures of the document(s) named above are incorporated herein by reference.

BACKGROUND OF THE INVENTION

1. Field of the Invention

The present invention relates to a polychloroprene latex, a rubber composition, and a dip-molded article. More specifically, it relates to a polychloroprene latex and a rubber composition used in dip molding and a dip-molded article prepared by using the same.

2. Description of the Related Art

Polychloroprene latexes, which are superior in mechanical strength, weather resistance, heat resistance, chemical resistance and others, have been used in various applications including dip-molded articles, textile processing agents, paper-coating agents, adhesives, bonding agents, high-elasticity asphalts (modified asphalts) and high-elasticity cements. In particular among dip-molded articles, polychloroprene latexes have been used as the primary raw material for various gloves for example for domestic, industrial, and medical uses (see, for example, Patent Document 1).

There was reported a polychloroprene latex for gloves, in which the 2-chloro-1,3-butadiene content and the 2,3-dichloro-1,3-butadiene content in the raw monomers are adjusted in particular ranges for improvement of the balance among stability of flexibility over time, tensile strength, and tensile elongation (see Patent Document 2). There were also proposed a polychloroprene latex for gloves, in which the monomer composition thereof, the tetrahydrofuran-insoluble matter content of the polymer, and the crystallization rate R are controlled in particular ranges (see Patent Document 3) and a chloroprene polymer latex for production of vulcanized rubbers, in which the 1 mass % toluene-insoluble matter content of the chloroprene polymer is adjusted in a particular range (see Patent Document 4).

CITATION LIST

Patent Literatures

[Patent Document 1] Japanese Unexamined Patent Application Publication No. 2010-144278
[Patent Document 2] Japanese Unexamined Patent Application Publication No. 2007-106994
[Patent Document 3 Japanese Unexamined Patent Application Publication No. 2011-122141
[Patent Document 4] Japanese Unexamined Patent Application Publication No. 2010-126586

SUMMARY OF THE INVENTION

Technical Problem

A polymeric surfactant that functions as antifreeze stabilizer is added to the conventional polychloroprene latexes described in Patent Documents 1 to 4 for improvement of low-temperature stability. However, addition of such a polymeric surfactant to the polychloroprene latex in a great amount disadvantageously leads to inhibition of aggregation of the rubber components and makes it difficult to produce a rubber film. Thus in the case of conventional polychloroprene latexes, a pH adjuster is added after all ingredients are added, to the composition to give a latex at pH 10.0 to 11.5 for improvement of the agglutinating property of the rubber component and for production of a rubber film having a thickness most suited to dip-molded articles.

Accordingly, a main object of the present invention is to provide a polychloroprene latex and a rubber composition that give a dip-molded article with favorable low-temperature stability without deterioration of the agglutinating property during production of the dip-molded article and a dip-molded article prepared by using the same.

Solution to Problem

The polychloroprene latex according to the present invention is a polychloroprene latex comprising a chloroprene copolymer prepared by polymerizing raw monomers at least containing chloroprene and 2,3-dichloro-1,3-butadiene, dispersed in water, wherein the 2,3-dichloro-1,3-butadiene content in the raw monomers is 1 to 30 mass %; and the potassium ion content in the polychloroprene latex is 0.7 to 1.5 parts by mass and the sodium ion content therein is controlled to 0.2 parts or less by mass with respect to 100 parts by mass of the solid matter.

The chloroprene copolymer may have a gel content of 30 to 95 mass %.

The chloroprene latex is produced, for example, by initiating the emulsion polymerization, as the monomer amount initially added is adjusted to 10 to 50 mass % with respect to all monomers, and continuing the emulsion polymerization by adding the remaining monomers, which are previously cooled to a temperature lower than the polymerization temperature, to the polymerization system continuously during the polymerization period of from a monomer conversion rate of 1 to 40% to the final conversion rate.

The rubber composition according to the present invention comprises the polychloroprene latex described above in an amount of 100 parts by mass as solid matter, a metal oxide in an amount of 1 to 10 parts by mass, sulfur in an amount of 0.1 to 3 parts by mass, an aging inhibitor in an amount of 0.1 to 5 parts by mass, and a surfactant in an amount of 0.1 to 10 parts by mass.

The dip-molded article according to the present invention is an article prepared by dip molding of the polychloroprene latex or the rubber composition described above and is, for example, disposable medical gloves.

Advantageous Effects of Invention

Because the chloroprene latex according to the present invention is prepared by polymerization of raw monomers containing 2,3-dichloro-1,3-butadiene in an amount of 1 to 30 mass % and the potassium ion content therein is a particular amount and the sodium ion content is controlled to be not larger than a particular amount, it is possible to provide the chloroprene latex with low-temperature stability, while preserving its favorable rubber agglutinating property during production of dip-molded articles.

Additional aspects and/or advantages of the invention will be set forth in part in the description which follows and, in part, will be obvious from the description, or may be learned by practice of the invention.

DESCRIPTION OF EMBODIMENTS

Hereinafter, favorable embodiments of the present invention will be described in detail. The present invention is not limited to the embodiment described below.

First Embodiment

First, the polychloroprene latex in the first embodiment of the present invention will be described. The polychloroprene latex of the present embodiment contains a copolymer of 2-chloro-1,3-butadiene (hereinafter, referred to as chloroprene) and 2,3-dichloro-1,3-butadiene or a copolymer of chloroprene, 2,3-dichloro-1,3-butadiene, and other monomers (hereinafter, such copolymers will be referred to as chloroprene copolymers collectively), as it is dispersed in water.

In the polychloroprene latex of the present embodiment, the amount of 2,3-dichloro-1,3-butadiene in the raw monomers is 1 to 30 mass %. Further in the polychloroprene latex in the present embodiment, the potassium ion content in the polychloroprene latex is 0.7 to 1.5 parts by mass and the sodium ion content is controlled to be not more than 0.2 part by mass with respect to 100 parts by mass of the solid matter.

[Chloroprene Copolymer]

In production of the polychloroprene latex of the present embodiment, chloroprene and 2,3-dichloro-1,3-butadiene are copolymerized for adjustment of the properties such as flexibility of the dip-molded article obtained. When the 2,3-dichloro-1,3-butadiene content in the raw monomers is less than 1 mass %, it is not possible to improve the crystallization resistance of the copolymer. Alternatively when the 2,3-dichloro-1,3-butadiene content in the raw monomers is more than 30 mass %, the chloroprene copolymer crystallizes excessively, leading to deterioration of flexibility.

The 2,3-dichloro-1,3-butadiene content in the raw monomers is preferably 5 to 20 parts by mass for improvement of crystallization resistance. A crystallization-resistant chloroprene copolymer, when used, gives dip-molded articles superior in flexibility and, for example, gloves and other articles superior in fitness when used. Dip-molded articles gradually become hardened after production, but the crystallization-resistant chloroprene copolymer, when used, is resistant to such a change over time.

Alternatively, the chloroprene copolymer contained in the polychloroprene latex of the present embodiment may be a copolymer of chloroprene, 2,3-dichloro-1,3-butadiene and other monomers. Here, the other monomers copolymerizable with chloroprene and 2,3-dichloro-1,3-butadiene include, for example, acrylate esters such as methyl acrylate, butyl acrylate, and 2-ethylhexyl acrylate; methacrylate esters such as methyl methacrylate, butyl methacrylate, and 2-ethylhexyl methacrylate; hydroxy (meth)acrylates such as 2-hydroxyethyl (meth)acrylate, 2-hydroxymethyl (meth)acrylate, and 2-hydroxypropyl (meth)acrylate; 1-chlorobutadiene, butadiene, isoprene, ethylene, styrene, acrylonitrile and the like.

These monomers may be used alone or in combination of two or more. When monomers other than chloroprene and 2,3-dichloro-1,3-butadiene are used for copolymerization, the monomers other than chloroprene are preferably used in a total amount of 1 to 30 mass %, more preferably of 5 to 20 mass %, for improvement of the flexibility of the resulting dip-molded article and also for preservation of the favorable properties of the chloroprene copolymer such as weather resistance, heat resistance, and chemical resistance.

The chloroprene copolymer contained in the polychloroprene latex of the present embodiment preferably has a gel content of 30 to 95 mass % for improvement of the strength of the dip-molded article and for prevention of shrinkage during dip molding. For example when the gel content of the chloroprene copolymer is less than 30 mass %, as the crosslinking density of the polymer in the latex particles is lower, the dip-molded article may not be crosslinked at sufficiently high density if it is vulcanized. Thus, the dip-molded article after vulcanization may have reduced modulus (elongation stress) and insufficient strength.

Alternatively when the gel content of the chloroprene copolymer is more than 95 mass %, the polymers in the latex particles may be crosslinked at excessively high density. In this case, when a dip-molded article is vulcanized, the difference between the crosslinking density of the polymers in the original latex particles and that of the latex particles becomes larger, and thus, the stress during deformation is applied mainly to the latex particles, which are lower in crosslinking density, leading to deterioration of mechanical properties such as breaking elongation and breaking strength. The gel content of the chloroprene copolymer is more preferably 40 to 85 mass % and it is possible, when it is in the range, to produce a dip-molded article superior in mechanical properties.

The gel content of the chloroprene copolymer can be determined by the following method: First, a polychloroprene latex is freeze-dried and the mass A (g) thereof is determined. The dried product obtained is then dissolved in toluene to a concentration of 0.6 mass % under the condition of a temperature of 23° C. for 20 hours. After solid liquid separation by centrifugal separator, the insoluble matter is separated with a 200-mesh wire mesh. The separated insoluble matter is dried in air and additionally in an atmosphere at 110° C. for 1 hour and the mass B (g) thereof is determined. The gel content is calculated according to the following Formula 1:

$$\text{Gel content (\%)} = (B/A) \times 100 \qquad \text{[Formula 1]}$$

The gel content of the chloroprene copolymer contained in the polychloroprene latex of the present embodiment can be adjusted, as the addition amount of the chain-transfer agent used during polymerization of the raw monomers and the monomer conversion rate are modified.

[Potassium Ion: 0.7 to 1.5 Parts by Mass with Respect to 100 Parts by Mass of Solid Matter]

When the potassium ion content in the polychloroprene latex is less than 0.7 part by mass with respect to 100 parts by mass of the solid matter, the latex has decreased low-temperature stability. As a result, the latex demands addition of an antifreeze stabilizer and the polychloroprene latex or the rubber composition has lower rubber agglutinating property during dip molding. Alternatively when the potassium ion content is more than 1.5 parts by mass with respect to 100 parts by mass of the solid matter in the polychloroprene latex, the latex is unstabilized, as the amount of the electrolyte becomes excessive.

Thus, the potassium ion content in the polychloroprene latex of the present embodiment is 0.7 to 1.5 parts by mass with respect to 100 parts by mass of the solid matter. The potassium ion content is preferable in the range of 1.0 to 1.3 parts by mass with respect to 100 parts by mass of the solid matter and it is thus possible to obtain a polychloroprene latex superior in low-temperature stability without addition of an antifreeze stabilizer.

Here, the potassium ion content in the polychloroprene latex can be determined, for example, by acidic decomposition of the polychloroprene latex in nitric acid and subsequent inductively coupled plasma atomic emission spectrochemical analysis (ICP-AES). The potassium ion content in the polychloroprene latex can be adjusted, as the reducing agent and the buffer salt used for acceleration of the polymerization are properly selected. For example for addition of potassium ions to the polychloroprene latex, a potassium salt such as potassium pyrosulfite, potassium sulfite, potassium hydrogen sulfite, potassium phosphate, and potassium hydrogen phosphate can be used as the reducing agent and the buffer salt.

[Sodium Ion: 0.2 Part or Less by Mass with Respect to 100 Parts by Mass of Solid Matter]

When the sodium ion content is more than 0.2 part by mass with respect to 100 parts by mass of the solid matter in the polychloroprene latex, the low-temperature stability of the latex declines. As a result, addition of an antifreeze stabilizer is needed and the rubber agglutinating property during dip molding of the polychloroprene latex or the rubber composition decreases. Thus in the polychloroprene latex of the present embodiment, the sodium ion content is adjusted to 0.2 part or less by mass with respect to 100 parts by mass of the solid matter. The sodium ion content in the polychloroprene latex is preferably smaller, and most preferably the polychloroprene latex does not contain any sodium ion.

Here, the sodium ion content in the polychloroprene latex can be determined, similarly to the potassium ion content, by acidic decomposition of polychloroprene latex with nitric acid and subsequent inductively coupled plasma atomic emission spectrochemical analysis (ICP-AES). The sodium ion content in the polychloroprene latex can also be adjusted, as the reducing agent and the buffer salt used for acceleration of the polymerization are properly selected.

[Production Method]

Hereinafter, the method for producing the polychloroprene latex of the present embodiment will be described. In production of the polychloroprene latex in the present embodiment, raw monomers in an amount of 10 to 50 mass % of all raw monomers are first fed and polymerized to a monomer conversion rate of 1 to 40% (first polymerization step). The polymerization is then continued to the final polymerization conversion rate, as the remaining raw monomers, which are previously cooled to a temperature lower than the polymerization temperature, are added to the polymerization system continuously (second polymerization step).

The method of polymerizing the monomers may, for example, be emulsion polymerization, solution polymerization, suspension polymerization, bulky polymerization or the like, but an emulsion polymerization method is particularly favorable for production of the polychloroprene latex of the present embodiment. The emulsifier or the dispersant used during emulsion polymerization of raw monomers may be an alkali-metal salt of common rosin acid, but a potassium salt of disproportionated rosin acid is preferably used to adjust the sodium and potassium ion contents in the ranges above.

The emulsifier or the dispersant may be a combination of the alkali-metal salt of rosin acid described above and a carboxylic acid-, sulfonic acid-, sulfate ester-, or phosphoric ester-type emulsifier or dispersant. Among the emulsifiers and dispersants usable in combination, the carboxylic acid-type emulsifiers and dispersants include, for example, fatty monocarboxylic acid salts, polyoxyethylene alkyl ether carboxylic acid salts, N-acylsarcosine salts, N-acylglutamic acid salts and the like.

The sulfonic acid-type emulsifiers and dispersants include, for example, dialkyl sulfosuccinate salts, alkanesulfonate salts, α-olefinsulfonate salts, linear alkylbenzenesulfonate salts, alkyl (branched)-benzenesulfonate salts, naphthalenesulfonate salt/formaldehyde condensates, alkylnaphthalenesulfonate salts, N-methyl-N-acyltaurine salts and the like. The sulfate ester-type emulsifiers and dispersants include, for example, alkyl sulfate ester salts, alcohol ethoxy sulfates, oil sulfate ester salts and the like. The phosphate ester-type emulsifiers and dispersants include, for example, alkyl phosphate salts, polyoxyethylene alkyl ether phosphate salts, polyoxyethylene alkylphenylether phosphate salts and the like.

The other usable emulsifiers and dispersants include alkylallylsulfonic acids, polyoxyethylene phenyl ethers, polyoxyalkylene alkyl ethers, polyoxyethylene alkylene alkyl ethers, polyoxyethylene styrenated phenyl ethers, polyoxyethylene distyrenated phenyl ethers, polyoxyethylene tribenzyl phenyl ethers, polyoxyethylene polyoxypropylene glycols, polyoxyalkylene alkenyl ethers, sorbitan fatty acid esters, polyoxyethylene sorbitan fatty acid esters and the like.

In the production method for the polychloroprene latex of the present embodiment, it is preferable to use an anionic emulsifier or dispersant, in particular, a potassium salt, among the emulsifiers and dispersants described above, for reduction of the sodium ion content in the polychloroprene latex. However, as the emulsifiers and dispersants other than the alkali-metal salt of rosin acid described above are used only in small amounts and thus have smaller influence on the sodium ion content in the polychloroprene latex, common sodium salts may be used.

The chain-transfer agent is not particularly limited and those commonly used in emulsion polymerization of chloroprene can be used. Typical examples thereof are known chain-transfer agents including long-chain alkylmercaptans such as n-dodecylmercaptan and tert-dodecylmercaptan, dialkylxanthogen disulfides such as diisopropylxanthogen disulfide and diethylxanthogen disulfide and iodoform.

The polymerization initiator that can be used is, for example, potassium persulfate, ammonium persulfate, sodium persulfate, hydrogen peroxide, or an organic peroxide such as benzoyl peroxide.

The polymerization temperature is also not particularly limited, but the polymerization is preferably carried out at a temperature in the range of 25 to 55° C., more preferably in the range of 30 to 50° C., for preservation of the stability over time of the flexibility of the chloroprene copolymer.

The monomer conversion rate by polymerization is preferably 80 to 95%, more preferably 85 to 95%. A polymerization conversion rate of less than 80% may lead to decrease of the solid matter content in the polymer latex and thus deterioration of productivity. Alternatively, a polymerization conversion rate of more than 95% may lead to elongation of the polymerization period, thus deterioration of productivity and also to deterioration of the mechanical strength and rigidity of the dip-molded article when formed.

The terminator added to terminate polymerization before the monomer conversion rate by polymerization reaches to 100% is, for example, thiodiphenylamine, 4-tertiary butyl catechol, 2,2-methylene bis-4-methyl-6-tertiary-butylphenol, diethylhydroxylamine or the like.

In the method for producing the polychloroprene latex of the present embodiment, as the raw monomers are added in a total amount of 10 to 50 mass % with respect to the total weight of all monomers at the time of the initial polymerization, and continued, as the remaining raw monomers, which are previously cooled to a temperature lower than the polymerization temperature, are added continuously over the period from the point of the monomer conversion rate of 1 to 40% to the point of the final polymerization conversion rate. It is possible in this way to remove the heat generated in the polymerization system effectively and carry out the polymerization reaction reliably in a short period of time.

A pH adjuster, an antifreeze stabilizer, an emulsion stabilizer, a viscosity improver, an antioxidant, an antiseptic and/ or the like may be added arbitrarily to the polychloroprene latex of the present embodiment in the range that does not impair the advantageous effects of the present invention, for improvement of colloid stability and other properties after polymerization.

As described above in detail, because the potassium ion content is controlled in the range of 0.7 to 1.5 parts by mass and the sodium ion content in the range of 0.2 part or less by mass with respect to 100 parts by mass of the solid matter in the polychloroprene latex of the present embodiment, it is possible to provide the chloroprene latex with improved low-temperature stability, while preserving the favorable rubber agglutinating property during production of the dip-molded article. In addition, the polychloroprene latex of the present embodiment has the basic properties inherent to polychloroprene and the molded article therefrom can show favorable flexibility for an extended period of time. Further, the polychloroprene latex of the present embodiment can be used for production of dip-molded rubber articles such as gloves and it is particularly favorably used for production of disposable medical gloves.

Second Embodiment

Hereinafter, the rubber composition in the second embodiment of the present invention will be described. The polychloroprene latex of the first embodiment described above can be used, as it is, as a material for dip-molded article. It is also possible to convert it into a rubber composition by adding various additives thereto. Specifically, the rubber composition of the present embodiment contains the polychloroprene latex of the first embodiment and additionally a metal oxide in an amount of 1 to 10 parts by mass, sulfur in an amount of 0.1 to 3 parts by mass, an aging inhibitor in an amount of 0.1 to 5 parts by mass, a surfactant in an amount of 0.1 to 10 parts by mass with respect to 100 parts by mass of the solid matter of the polychloroprene latex.

[Metal Oxide: 1 to 10 Parts by Mass with Respect to 100 Parts by Mass of Solid Matter]

The metal oxide added is not particularly limited and may be, for example, zinc oxide, lead oxide, trilead tetraoxide or the like. These compounds may be used alone or, as needed, in combination of two or more.

The amount of these metal oxides blended is 1 to 10 parts by mass with respect to 100 parts by mass of the solid matter of the polychloroprene latex. A metal oxide blending amount of less than 1 part by mass with respect to 100 parts by mass of the solid matter leads to insufficient crosslinking and gives a molded article insufficient in basic properties including tensile strength and modulus. Alternatively a metal oxide blending amount of more than 10 parts by mass with respect to 100 parts by mass of the solid matter leads to excessively high modulus of the molded article and gives gloves, if formed, with coarse touch feeling.

[Sulfur: 0.1 to 3 Parts by Mass with Respect to 100 Parts by Mass of Solid Matter]

Sulfur is added for acceleration of vulcanization. However when the sulfur blending amount is less than 0.1 part by mass with respect to 100 parts by mass of the solid matter, it is not possible to obtain sufficiently high vulcanization-accelerating effect. Alternatively when the sulfur blending amount is more than 3 parts by mass with respect to 100 parts by mass of the solid matter, the vulcanization is accelerated too much, leading to easier scorching, making it difficult to control the vulcanization and giving a vulcanized product with lower heat resistance or with an appearance damaged by bleeding. Thus, the sulfur blending amount is 0.1 to 3 parts by mass with respect to 100 parts by mass of the solid matter of the polychloroprene latex.

[Aging Inhibitor: 0.1 to 5 Parts by Mass with Respect to 100 Parts by Mass of Solid Matter]

For use in applications demanding extremely high heat resistance, it is needed to use an aging inhibitor for providing heat resistance (heat-resistant aging inhibitor) or an aging inhibitor for providing ozone-resistance (ozone-resistant aging inhibitor). It is more preferable to use both of them. The heat-resistant aging inhibitor is desirably resistant to heat and also to staining (which leads to discoloration), and favorable examples thereof include diphenylamine-based compound such as octylated diphenylamines, p-(p-toluene-sulfonylamido)diphenylamine, and 4,4'-bis($\alpha$,$\alpha$-dimethylbenzyl) diphenylamine.

Alternatively, the ozone-resistant aging inhibitor is preferably N,N'-diphenyl-p-phenylenediamine (DPPD) or N-isopropyl-N'-phenyl-p-phenylenediamine (IPPD). However, hindered phenol-based aging inhibitors are preferable, when the appearance, in particular the color tone and the hygiene of the article are considered important, as in medical gloves.

The amount of the aging inhibitor added is 0.1 to 5 parts by mass with respect to 100 parts by mass of the solid matter of the polychloroprene latex. An aging inhibitor blending amount of less than 0.1 part by mass with respect to 100 parts by mass of the solid matter leads to insufficient anti-aging effect. Alternatively an aging inhibitor blending amount of more than 5 parts by mass with respect to 100 parts by mass of the solid matter leads to inhibition of vulcanization and deterioration in color tone.

[Surfactant: 0.1 to 10 Parts by Mass with Respect to 100 Parts by Mass of Solid Matter]

Examples of the surfactant for use include sodium alkylsulfates, sodium alkylbenzenesulfonate, sodium salts of naphthalenesulfonic acid/formaldehyde condensates, rosin acid soaps, fatty acid soaps and the like. The amount of these surfactants blended is 0.1 to 10 parts by mass with respect to 100 parts by mass of the solid matter of the polychloroprene latex. A surfactant blending amount of less than 0.1 parts by mass with respect to 100 parts by mass of the solid matter leads to insufficient colloid stabilization. Alternatively a surfactant blending amount of more than 10 parts by mass with respect to 100 parts by mass of the solid matter leads to foaming and deterioration in article appearance such as pinholes.

Surfactants insoluble in water or unstabilizing the colloidal state of the polychloroprene latex among the surfactants described above may be added to the polychloroprene latex in the form of aqueous dispersion, as it is prepared in advance.

In addition to the components described above, various additives such as vulcanization accelerators, pH adjusters, fillers, plasticizers, pigments, colorants, wetting agents, and antifoams may be added, as needed, to the rubber composition of the present embodiment.

As described above in detail, the rubber composition of the present embodiment, which employs the polychloroprene latex of the first embodiment described above, is superior in low-temperature stability and also in rubber agglutinating property during production of dip-molded articles. The rubber composition of the present embodiment can be processed by dip molding into any shape and is particularly favorably used in production of disposable medical gloves.

Third Embodiment

Hereinafter, the dip-molded article in the third embodiment of the present invention will be described. The dip-molded article of the present embodiment is an article prepared by dip molding of the chloroprene latex of the first embodiment or the rubber composition of the second embodiment described above. It is, for example, disposable medical gloves.

The method for producing dip-molded article of the present embodiment is not particularly limited and the dip-molded article can be prepared by dip molding and vulcanization by common methods. Specifically, a molding mold previously coated with a coagulant is immersed in a polychloroprene latex or a rubber composition for coagulation. Water-soluble impurities in the resulting film are removed by leaching; the film is dried and then vulcanized; and the rubber film obtained is separated, to give a film-shaped dip-molded article.

The thickness of the dip-molded article of the present embodiment can be adjusted by modifying the time of the molding mold immersed into the polychloroprene latex or the rubber composition, or by modifying the solid concentration of the polychloroprene latex or the rubber composition. Specifically if the dip-molded article is desirably thinner, the immersion time may be shortened or the solid concentration of the polychloroprene latex or the rubber composition adjusted to be lower.

As described above in detail, the dip-molded article of the present embodiment, which is prepared from the polychloroprene latex of the first embodiment or the rubber composition of the second embodiment described above, is superior in flexibility and also resistant to deterioration in flexibility over time.

EXAMPLES

Hereinafter, the advantageous effects of the present invention will be described specifically with reference to Examples and Comparative Examples of the present invention. However, it should be understood that the present invention is not restricted by these Examples. In the following Examples, polychloroprene latexes of Examples and Comparative Examples were prepared and the properties thereof evaluated by the methods below.

Example 1

<Polychloroprene Latex> water: 100 parts by mass, potassium salt of a disproportionated rosin acid (Rondis K-25, produced by Arakawa Chemical Industries): 2.5 parts by mass, potassium hydroxide: 0.8 part by mass, sodium salt of a naphthalenesulfonic acid/formaldehyde condensate (Demol N, manufactured by Kao Corporation): 0.8 part by mass, and potassium sulfite: 0.5 part by mass were placed and dissolved in a reactor having a capacity of 10 liters under nitrogen stream and chloroprene: 90 parts by mass, 2,3-dichloro-1,3-butadiene: 10 parts by mass, and n-dodecylmercaptan: 0.14 parts by mass were added thereto, as the mixture was agitated.

The mixture was polymerized, using potassium persulfate as initiator, under nitrogen environment at 40° C. and the polymerization was terminated by addition of a phenothiazine emulsion when the polymerization rate reached 90%. Unreacted monomers were removed then under reduced pressure, to give a polychloroprene latex. Further, the polychloroprene latex was concentrated, as water was evaporated under reduced pressure, to a solid matter content therein of 60 mass %.

[Amount of Alkali-Metal Salt]

The polychloroprene latex (1.0 g) was acidically decomposed with mixed sulfuric and nitric acid; the decomposition product was acidified with hydrochloric acid and the alkali-metal salt content therein was determined quantitatively on an inductively coupled plasma atomic emission spectrochemical analyzer produced by SII Nano Technology (ICP-AES: VISTA-PRO).

[Content of 2,3-dichloro-1,3-butadiene]

The polychloroprene latex was freeze-dried and the content of 2,3-dichloro-1,3-butadiene was determined quantitatively, using a pyrolyzer produced by Japan Analytical Industry (JPS-330) and a gas chromatograph produced by Agilent Technologies (HP5890-II).

[Gel Content]

The polychloroprene latex was freeze-dried and the mass A (g) was determined. The dried polychloroprene latex obtained was then dissolved in toluene under the condition of a temperature of 23° C. for 20 hours to a concentration of 0.6 mass %. The solution was separated to liquid and solid in a centrifugal separator and the insoluble matter was separated with a 200-mesh wire mesh. The insoluble matter separated was dried in air and additionally in an atmosphere at 110° C. for 1 hour, and the mass B (g) was determined. The toluene insoluble matter content was calculated according to Formula 1 above.

[Low-Temperature Stability of Polychloroprene Latex]

The polychloroprene latex was left in an atmosphere at 5° C. for a week and additionally in an atmosphere at 0° C. for a day and the appearance of respective polychloroprene latexes was observed visually. A polychloroprene latex without change in appearance was indicated by ○, that with increased viscosity by Δ, and that with coagulation or coagulum by x.

[Aggregation Property of Polychloroprene Latex]

50 ml of saturated aqueous calcium hydroxide solution was added dropwise to 50 g of the polychloroprene latex and the resulting mixture was left still at 20° C. for 16 hours. The precipitated rubber was dried at 110° C. for 3 hours and the rubber aggregation rate of the polychloroprene latex was determined.

[Film Texture]

The texture of the film was evaluated from the difference in hardness of the dry films stored at 0° C. for 150 hours. The texture of the film when the change in hardness from the initial hardness is less than 50 was indicated by ⊚), the texture of the film when it is 50 or more and less than 80 by ○ and the texture of the film when it is 80 or more by x.

<Rubber Composition>

The compounds shown in the following Table 1 were added to the polychloroprene latex having a solid matter content of 60 mass % obtained by the method described above, to give a rubber composition. The aging inhibitor used then was Nocrac 200 manufactured by Ouchi Shinko Chemical Industrial. The vulcanization accelerator A used was Nocceler TP manufactured by Ouchi Shinko Chemical Industrial (sodium dibutyl dithiocarbamate) and the vulcanization accelerator B used was Nocceler TET manufactured by Ouchi Shinko Chemical Industrial (tetraethylthiuram disulfide). The surfactant A used was Darvan SMO manufactured by R. T. Vanderbilt Company and the surfactant B used was Darvan WAQ manufactured by R. T. Vanderbilt Company.

TABLE 1

|  | Parts by mass |
|---|---|
| Chloroprene latex | 100 |
| No. 2 zinc white | 5 |

TABLE 1-continued

|  | Parts by mass |
|---|---|
| Aging inhibitor | 2 |
| Sulfur | 1 |
| Vulcanization accelerator A | 1 |
| Vulcanization accelerator B | 1 |
| Surfactant A | 3 |
| Surfactant B | 1 |

<Unvulcanized Film>

An immersion film of the rubber composition was prepared from the rubber composition, using the primary and secondary coagulants shown in the following Table 2. The primary coagulant accelerates coagulation of the dip-molding solution into the film shape. The immersion film was prepared in the following manner: A test tube having a outer diameter of 40 mm and a length of 320 mm was immersed with its opening facing upward into the primary coagulant for 10 seconds to a depth of 150 mm and dried in air for 3 minutes. It is then immersed into the rubber composition for 1 minute, forming an immersion film on the surface of the test tube. Water-soluble components in the immersion film obtained were removed, as the film was leached with running water for 1 minute. The test tube was additionally immersed into the secondary coagulant for 1 minute and then leached with running water for removal of the secondary coagulant on the surface of the immersion film. It was then dried at 70° C. for 2 hours, to give an unvulcanized film.

TABLE 2

|  | Primary coagulant | Secondary coagulant |
|---|---|---|
| Calcium nitrate (tetrahydrate) | 30 | — |
| Methanol | 70 | 50 |
| Bentonite | 30 | — |
| Acetic acid (20% aqueous solution) | — | 50 |

[Unvulcanized Film-Forming Efficiency]

The unvulcanized film was separated from test tube and the appearance of the film was observed visually. A film favorable in appearance was indicated by 0, while that for example with rupture by x.

[Physical Properties of Vulcanized Film]

The unvulcanized film was vulcanized at 141° C. for 30 minutes into a vulcanized film and cut into test pieces in the dumbbell No. 3 shape according to the method of JIS K6251. The modulus at 300% extension, the breaking elongation and the breaking strength of the test piece were determined, using a tensile tester (Quick Reader mx) produced by Ueshima Seisakusho.

Examples 2 to 11 and Comparative Examples 1 to 6

Polychloroprene latexes, rubber compositions, and film samples were prepared by methods similar to those used in Example 1 respectively in the compositions shown in the following Tables 3 to 5 and evaluated similarly to Example 1. The evaluation results are summarized in Tables 3 to 5. The polychloroprene latex of Example 2 was prepared, as chloroprene: 21 parts by mass, 2,3-dichloro-1,3-butadiene: 9 parts by mass, and n-dodecylmercaptan: 0.042 part by mass were first polymerized and chloroprene: 63 parts by mass, 2,3-dichloro-1,3-butadiene: 7 parts by mass, and n-dodecylmercaptan: 0.098 part by mass were added thereto for further polymerization, when the polymerization rate reached 10%.

TABLE 3

|  |  |  | Example 1 | Example 2 | Example 3 | Example 4 | Example 5 |
|---|---|---|---|---|---|---|---|
| Initially added | Chloroprene | (mass %) | 90 | 27 | 90 | 90 | 90 |
|  | 2,3-Dichloro-1,3-butadiene | (mass %) | 10 | 3 | 10 | 10 | 10 |
|  | n-Dodecylmercaptan | (mass %) | 0.14 | 0.042 | 0.14 | 0.14 | 0.2 |
| Separately added | Chloroprene | (mass %) |  | 63 |  |  |  |
|  | 2,3-Dichloro-1,3-butadiene | (mass %) |  | 7 |  |  |  |
|  | n-Dodecylmercaptan | (mass %) |  | 0.098 |  |  |  |
| Emulsifier | H$_2$O | (mass %) | 100 | 100 | 100 | 100 | 100 |
|  | Rosin acid sodium | (mass %) |  |  |  | 0.5 |  |
|  | Rosin acid potassium | (mass %) | 2.5 | 2.5 | 4 | 3.5 | 2.5 |
|  | KOH | (mass %) | 0.75 | 0.75 | 0.5 | 0.5 | 0.75 |
| Dispersant | Naphthalenesulfonic acid/formaldehyde condensate | (mass %) | 0.8 | 0.8 | 0.8 | 0.3 | 0.8 |
| Reducing agent | Sodium bisulfite | (mass %) |  |  |  |  |  |
|  | Potassium pyrosulfite | (mass %) | 0.5 | 0.5 | 0.5 | 0.5 | 0.5 |
| Stabilizer | Polyoxyethylene cetyl ether | (mass %) |  |  |  |  |  |
| Alkali-metal salt content (parts by mass, with respect to 100 parts by mass of solid matter) | Na |  | 0.08 | 0.08 | 0.08 | 0.09 | 0.08 |
|  | K |  | 1.1 | 1.1 | 1.09 | 1.03 | 1.1 |
| 2,3-Dichloro-1,3-butadiene content |  | (mass %) | 10.7 | 10.6 | 10.7 | 10.5 | 10.8 |
| Toluene-insoluble matter content in polychloroprene latex |  | (mass %) | 82 | 84 | 82 | 83 | 35 |
| Polychloroprene latex Low-temperature stability | 5° C. |  | ○ | ○ | ○ | ○ | ○ |
|  | 0° C. |  | ○ | ○ | ○ | ○ | ○ |
| Polychloroprene latex Agglutinating property |  |  | 40% | 39% | 25% | 24% | 38% |

TABLE 3-continued

|  |  | Example 1 | Example 2 | Example 3 | Example 4 | Example 5 |
|---|---|---|---|---|---|---|
| Polychloroprene latex Film texture | | ◎ | ◎ | ◎ | ◎ | ◎ |
| Polychloroprene latex composition Film-forming efficiency | | ○ | ○ | ○ | ○ | ○ |
| Physical properties of vulcanized film (vulcanization: 141° C. × 30 minutes) | | | | | | |
| Breaking elongation | (%) | 1090 | 1020 | 1130 | 1150 | 1140 |
| Breaking strength | (MPa) | 22.5 | 21.8 | 22.1 | 22 | 20.5 |
| 300% modulus | (MPa) | 1.21 | 1.19 | 1.16 | 1.19 | 1.02 |

TABLE 4

| | | | Example 6 | Example 7 | Example 8 | Example 9 | Example 10 | Example 11 |
|---|---|---|---|---|---|---|---|---|
| Initially added | Chloroprene | (mass %) | 90 | 80 | 95 | 90 | 90 | 90 |
| | 2,3-Dichloro-1,3-butadiene | (mass %) | 10 | 20 | 5 | 10 | 10 | 10 |
| | n-Dodecylmercaptan | (mass %) | 0.12 | 0.14 | 0.14 | 0.14 | 0.22 | 0.11 |
| Separately added | Chloroprene | (mass %) | | | | | | |
| | 2,3-Dichloro-1,3-butadiene | (mass %) | | | | | | |
| | n-Dodecylmercaptan | (mass %) | | | | | | |
| Emulsifier | H$_2$O | (mass %) | 100 | 100 | 100 | 100 | 100 | 100 |
| | Rosin acid sodium | (mass %) | | | | | | |
| | Rosin acid potassium | (mass %) | 2.5 | 2.5 | 2.5 | 2.5 | 2.5 | 2.5 |
| | KOH | (mass %) | 0.75 | 0.75 | 0.75 | 0.75 | 0.75 | 0.75 |
| Dispersant | Naphthalenesulfonic acid/formaldehyde | (mass %) | 0.8 | 0.8 | 0.8 | 0.8 | 0.8 | 0.8 |
| Reducing agent | Sodium bisulfite | (mass %) | | | | 0.5 | | |
| | Potassium pyrosulfite | (mass %) | 0.5 | 0.5 | 0.5 | | 0.5 | 0.5 |
| Stabilizer | Polyoxyethylene cetyl ether | (mass %) | | | | 0.2 | | |
| Alkali-metal salt content (parts by mass, with respect to 100 parts by mass of solid matter) | Na | | 0.08 | 0.08 | 0.08 | 0.17 | 0.08 | 0.08 |
| | K | | 1.1 | 1.1 | 1.1 | 0.9 | 1.1 | 1.1 |
| 2,3-Dichloro-1,3-butadiene content | | (mass %) | 10.6 | 21.3 | 5.2 | 10.7 | 10.6 | 10.5 |
| Toluene-insoluble matter content in polychloroprene latex | | (mass %) | 94 | 82 | 85 | 83 | 28 | 97 |
| Polychloroprene latex Low-temperature stability | | 5° C. | ○ | ○ | ○ | ○ | ○ | ○ |
| | | 0° C. | ○ | ○ | ○ | Δ | ○ | ○ |
| Polychloroprene latex Agglutinating property | | | 40% | 38% | 39% | 18% | 38% | 40% |
| Polychloroprene latex Film texture | | | ◎ | ○ | ○ | ◎ | ◎ | ◎ |
| Polychloroprene latex composition Film-forming efficiency | | | ○ | ○ | ○ | ○ | ○ | ○ |
| Physical properties of vulcanized film (vulcanization: 141° C. × 30 minutes) | | | | | | | | |
| Breaking elongation | | (%) | 990 | 1000 | 970 | 930 | 1250 | 890 |
| Breaking strength | | (MPa) | 20.1 | 20.9 | 21.2 | 20.8 | 19.8 | 18.9 |
| 300% modulus | | (MPa) | 1.23 | 1.18 | 1.22 | 1.16 | 0.98 | 1.25 |

TABLE 5

| | | | Comparative Example 1 | Comparative Example 2 | Comparative Example 3 | Comparative Example 4 | Comparative Example 5 | Comparative Example 6 |
|---|---|---|---|---|---|---|---|---|
| Initially added | Chloroprene | (mass %) | 100 | 68 | 90 | 90 | 90 | 90 |
| | 2,3-Dichloro-1,3-butadiene | (mass %) | | 32 | 10 | 10 | 10 | 10 |
| | n-Dodecylmercaptan | (mass %) | 0.14 | 0.14 | 0.14 | 0.14 | 0.14 | 0.14 |
| Separately added | Chloroprene | (mass %) | | | | | | |
| | 2,3-Dichloro-1,3-butadiene | (mass %) | | | | | | |
| | n-Dodecylmercaptan | (mass %) | | | | | | |
| Emulsifier | H$_2$O | (mass %) | 100 | 100 | 100 | 100 | 100 | 100 |
| | Rosin acid sodium | (mass %) | | | 0.5 | | 1.2 | 0.5 |
| | Rosin acid potassium | (mass %) | 2.5 | 2.5 | 1.5 | 4 | 2.8 | 3.5 |
| | KOH | (mass %) | 0.75 | 0.75 | 0.5 | 1 | 0.8 | 0.75 |
| Dispersant | Naphthalenesulfonic acid/formaldehyde condensate | (mass %) | 0.8 | 0.8 | 0.3 | 0.8 | 0.8 | 0.8 |

TABLE 5-continued

|  |  |  | Comparative Example 1 | Comparative Example 2 | Comparative Example 3 | Comparative Example 4 | Comparative Example 5 | Comparative Example 6 |
|---|---|---|---|---|---|---|---|---|
| Reducing agent | Sodium bisulfite | (mass %) |  |  |  |  |  | 0.5 |
|  | Potassium pyrosulfite | (mass %) | 0.5 | 0.5 | 0.25 | 0.6 | 0.5 |  |
| Stabilizer | Polyoxyethylene cetyl ether | (mass %) |  |  |  |  |  | 0.5 |
| Alkali-metal salt content (parts by mass, with respect to 100 parts by mass of solid matter) | Na |  | 0.8 | 0.8 | 0.09 | 0.08 | 0.22 | 0.23 |
|  | K |  | 1.1 | 1.1 | 0.68 | 1.52 | 1.13 | 1.03 |
| 2,3-Dichloro-1,3-butadiene content |  | (mass %) | 0 | 34.1 | 10.5 | 10.7 | 10.6 | 10.6 |
| Toluene-insoluble matter content in polychloroprene latex |  | (mass %) | 85 | 83 | 87 | 85 | 87 | 83 |
| Polychloroprene latex Low-temperature stability | 5° C. |  | ○ | ○ | Δ | Δ | X | ○ |
|  | 0° C. |  | ○ | ○ | X | X | X | ○ |
| Polychloroprene latex Agglutinating property |  |  | 40% | 40% | 42% | 23% | 27% | 12% |
| Polychloroprene latex Film texture |  |  | X | X | ◎ | ◎ | ◎ | ◎ |
| Polychloroprene latex composition Film-forming efficiency |  |  | ○ | ○ | ○ | ○ | ○ | X |
| Physical properties of vulcanized film (vulcanization: 141° C. × 30 minutes) |  |  |  |  |  |  |  |  |
| Breaking elongation |  | (%) | 1020 | 930 | 980 | 1120 | 1100 | — |
| Breaking strength |  | (MPa) | 20.8 | 20.6 | 20.9 | 22 | 21.8 | — |
| 300% modulus |  | (MPa) | 1.16 | 1.01 | 1.21 | 1.17 | 1.19 | — |

As shown in Table 5, because the polychloroprene latex used in Comparative Example 1 contained a homopolymer of chloroprene, the dry film obtained therefrom showed significant increase in hardness and had insufficient film texture. Alternatively in Comparative Example 2, because the polychloroprene latex contained a copolymer prepared from raw monomers containing 2,3-dichloro butadiene in an amount of more than 30 mass %, the dry film obtained showed significant increase in hardness and had insufficient film texture.

Alternatively in Comparative Example 3, as the potassium ion content in the polychloroprene latex is less than 0.7 part by mass with respect to 100 parts by mass of the solid matter, the latex showed insufficient low-temperature stability. Specifically, the polychloroprene latex of Comparative Example 3 showed increase in viscosity in an atmosphere at 5° C. and coagulated in an atmosphere of 0° C. Alternatively in Comparative Example 4, because the potassium ion content in the polychloroprene latex was more than 1.5 parts by mass with respect to 100 parts by mass of the solid matter, the latex showed insufficient low-temperature stability.

Alternatively in Comparative Example 5, because the sodium ion content in the polychloroprene latex was more than 0.2 parts by mass with respect to 100 parts by mass of the solid matter, the latex showed insufficient low-temperature stability. Yet alternatively in Comparative Example 6, because the sodium ion content in the polychloroprene latex was more than 0.2 parts by mass with respect to 100 parts by mass of the solid matter but an antifreeze stabilizer polyoxyethylene cetyl ether was added, the latex showed favorable low-temperature stability. However, the polychloroprene latex of Comparative Example 6 showed lower agglutinating property and it was not possible to produce a film for evaluation from the rubber composition.

In contrast, as shown in Tables 3 and 4, the polychloroprene latexes and rubber compositions of Example 1 to 11 prepared within the scope of the present invention showed favorable properties in all items. The results confirm that, according to the present invention, it is possible to provide a polychloroprene latex superior in both low-temperature stability and rubber agglutinating property during production of the dip-molded article.

Although a few embodiments of the present invention have been shown and described, it would be appreciated by those skilled in the art that changes may be made in this embodiment without departing from the principles and spirit of the invention, the scope of which is defined in the claims and their equivalents.

The invention claimed is:

1. A polychloroprene latex comprising a chloroprene copolymer prepared by polymerizing raw monomers at least containing chloroprene and 2,3-dichloro-1,3-butadiene, dispersed in water, wherein
 the 2,3-dichloro-1,3-butadiene content in the raw monomers is 1 to 30 mass %: and the potassium ion content in the polychloroprene latex is 0.9 to 1.1 parts by mass and the sodium ion content in the polychloroprene latex is 0.08 to 0.17 parts by mass with respect to 100 parts by mass of the solid matter.

2. The polychloroprene latex according to claim 1, wherein the chloroprene copolymer has a gel content of 30 to 95 mass %.

3. The polychloroprene latex according to claim 1, prepared by initiating emulsion polymerization, as the monomer amount initially added is adjusted to 10 to 50 mass % with respect to all monomers, and continuing the emulsion polymerization by adding the remaining monomers, which are cooled to a temperature lower than the polymerization temperature, to the polymerization system continuously during the polymerization period of from a monomer conversion rate of 1 to 40% to the final conversion rate.

4. A rubber composition, comprising the polychloroprene latex according to claim 1, in an amount of 100 parts by mass as solid matter,
 a metal oxide in an amount of 1 to 10 parts by mass,
 sulfur in an amount of 0.1 to 3 parts by mass,
 an aging inhibitor in an amount of 0.1 to 5 parts by mass, and
 a surfactant in an amount of 0.1 to 10 parts by mass.

5. A dip-molded article, prepared by dip molding, using the polychloroprene latex according to claim 1.

6. The dip-molded article according to claim 5, which is disposable medical gloves.

7. A rubber composition, comprising the polychloroprene latex according to claim 2, in an amount of 100 parts by mass as solid matter,
   a metal oxide in an amount of 1 to 10 parts by mass,
   sulfur in an amount of 0.1 to 3 parts by mass,
   an aging inhibitor in an amount of 0.1 to 5 parts by mass, and
   a surfactant in an amount of 0.1 to 10 parts by mass.

8. A rubber composition, comprising the polychloroprene latex according to claim 3, in an amount of 100 parts by mass as solid matter,
   a metal oxide in an amount of 1 to 10 parts by mass,
   sulfur in an amount of 0.1 to 3 parts by mass,
   an aging inhibitor in an amount of 0.1 to 5 parts by mass, and
   a surfactant in an amount of 0.1 to 10 parts by mass.

9. A dip-molded article, prepared by dip molding, using the rubber composition according to claim 4.

10. The dip-molded article according to claim 9, which is disposable medical gloves.

11. A dip-molded article, prepared by dip molding, using the polychloroprene latex according to claim 2.

12. A dip-molded article, prepared by dip molding, using the polychloroprene latex according to claim 3.

* * * * *